United States Patent
Himmler et al.

(10) Patent No.: US 10,150,731 B2
(45) Date of Patent: Dec. 11, 2018

(54) METHOD FOR PREPARING 4-CYANOPIPERIDINE HYDROCHLORIDE

(71) Applicant: BAYER CROPSCIENCE AKTIENGESELLSCHAFT, Monheim am Rhein (DE)

(72) Inventors: Thomas Himmler, Odenthal (DE); Dirk Brohm, Mettmann (DE)

(73) Assignee: BAYER CROPSCIENCE AKTIENGESELLSCHAFT, Monehim am Rhein (DE)

( * ) Notice: Subject to any disclaimer, the term of this patent is extended or adjusted under 35 U.S.C. 154(b) by 0 days.

(21) Appl. No.: 15/542,715

(22) PCT Filed: Jan. 13, 2016

(86) PCT No.: PCT/EP2016/050514
§ 371 (c)(1),
(2) Date: Jul. 11, 2017

(87) PCT Pub. No.: WO2016/113277
PCT Pub. Date: Jul. 21, 2016

(65) Prior Publication Data
US 2017/0369442 A1    Dec. 28, 2017

(30) Foreign Application Priority Data
Jan. 16, 2015   (EP) .................................... 15151468

(51) Int. Cl.
C07D 211/62   (2006.01)
(52) U.S. Cl.
CPC .................. C07D 211/62 (2013.01)
(58) Field of Classification Search
CPC .................................................. C07D 211/62
See application file for complete search history.

(56) References Cited

U.S. PATENT DOCUMENTS

| | | | | |
|---|---|---|---|---|
| 3,551,431 A * | 12/1970 | Kuhnis | ................ | C07D 211/62 514/849 |
| 5,948,786 A * | 9/1999 | Fujiwara | ............... | A61K 31/506 514/274 |
| 6,248,755 B1 * | 6/2001 | Chapman | ............. | C07D 401/06 514/252.13 |
| 7,348,435 B2 * | 3/2008 | Kaushik | ............... | C07D 211/62 546/246 |
| 7,888,374 B2 * | 2/2011 | Liu | ...................... | C07D 213/73 514/332 |
| 8,569,337 B2 * | 10/2013 | Jimenez | ............... | C07D 471/04 514/303 |
| 8,642,634 B2 * | 2/2014 | Pasteris | ................ | C07D 401/14 514/365 |
| 8,829,007 B2 * | 9/2014 | Charifson | ............ | A61K 31/506 514/256 |
| 2006/0084808 A1 | 4/2006 | Kaushik et al. | | |
| 2012/0040998 A1 * | 2/2012 | Mercer | ................ | C07D 413/04 514/255.05 |

OTHER PUBLICATIONS

Lawton "Synthesis of Pyromellitonitrile and Related Compounds" Journal of Organic Chemistry 1959, 24, 26.*
Bargar "Rapid and efficient method for dehydration of primary amides to nitriles. Preparation of acrylonitrile derivatives" Synthetic Communications (1980), 10(6), 479-87.*
Bollyn "Thermal Hazards of the Vilsmeier-Haack Reaction on N,N-Dimethylaniline" Org. Process Res. Dev. 2005, 9, 982.*
Orjales "Syntheses and Binding Studies of New [(Aryl)(aryloxy)methyl]piperidine Derivatives and Related Compounds as Potential Antidepressant Drugs with High Affinity for Serotonin (5-HT) and Norepinephrine (NE) Transporters" J. Med. Chem. 2003, 46, 5512-5532.*
Heinz Langhals et al: "Alkylwanderungen 1-7 bei Sextettumlagerungen I ) Migration of Alkgl Groups in Sextett Rearrangements I) Die Ladungsvertei", Ruchardt Chem. Ber, vol. 114, No. 12, Jan. 1, 1981 (Jan. 1, 1981), pp. 3813-3830, XP05517787.
International Search Report of PCT/EP2016/050514 dated Feb. 16, 2016.

* cited by examiner

Primary Examiner — David K O'Dell
(74) Attorney, Agent, or Firm — McBee Moore Woodward & Vanick IP, LLC

(57) ABSTRACT

The present invention describes a novel method for preparing 4-cyanopiperidine hydrochloride.

20 Claims, No Drawings

METHOD FOR PREPARING 4-CYANOPIPERIDINE HYDROCHLORIDE

CROSS REFERENCE TO RELATED APPLICATIONS

This application is a § 371 National State Application of PCT/EP2016/050514, filed Jan. 13, 2016, which claims priority to German Application No. 15151468.4 filed Jan. 16, 2015.

BACKGROUND OF THE INVENTION

Field of the Invention

The present invention relates to a novel method for preparing 4-cyanopiperidine hydrochloride.

Description of Related Art

4-Cyanopiperidine (CAS No. 4395-98-6) is an important intermediate for the preparation of active ingredients having pharmaceutical efficacy (for example, see U.S. Pat. No. 8,642,634; DE 3031892; J. Med. Chem. 46 (2003) 5512-32; WO 2004/092124; WO 2009/016410; WO 2010/104899) and of agrochemical active ingredients (WO 2013/098229). In many syntheses, instead of 4-cyanopiperidine, salts thereof such as the hydrochloride (CAS No. 240402-22-3) or the trifluoroacetate (CAS No. 904312-79-4) can in principle also be used, for example, by adding an organic or inorganic base so that the free 4-cyanopiperidine is liberated in situ.

Various preparation methods are already known for preparing 4-cyanopiperidine. For instance, U.S. Pat. No. 5,780,466 describes the dehydration of piperidine-4-carboxamide (isonipecotamide) by phosphorus oxychloride ($POCl_3$). The crude 4-cyanopiperidine hydrochloride thus obtained is taken up in water, the aqueous phase is adjusted to pH 13 with conc. aqueous sodium hydroxide solution and firstly extracted by shaking with methylene chloride and then repeatedly with ether. After drying the combined organic phases and removal of the solvents, the remaining oil is also distilled. The yield is 29.7% of theory. Disadvantages of this method are the laborious workup by multiple extraction with different organic solvents and the resulting very poor yield. In a further known method (DE 3031892), isonipecotamide is dehydrated by heating in trifluoroacetic anhydride. However, the 1-trifluoroacetyl-4-cyanopiperidine formed in this case must be converted to 4-cyanopiperidine in a second reaction step by hydrolysis in the presence of potassium carbonate. Finally, the resulting 4-cyanopiperidine is extracted from an aqueous solution with methylene chloride, the methylene chloride is distilled off and the crude 4-cyanopiperidine is distilled. The yield of 27.1% of theory is not in line with the requirements of an industrial process. The preparation of 4-cyanopiperidine by dehydrating isonipecotamide with thionyl chloride is described in Example 24, step A, in WO 2010/104899. In this case, the reaction mixture is added to an excess of ice, the resulting solution is adjusted to pH 9 with potassium hydroxide and then further concentrated. The residue thus obtained is extracted repeatedly with chloroform. After removal of the chloroform, a yield of only 36% is obtained. Disadvantages of this method are the large amount of thionyl chloride (6 mol equivalents), the necessity after quenching to neutralize a large amount of acid, the laborious extraction of the product using a volatile solvent and the low yield obtained. A very similar method is described in J. Med. Chem. 46 (2003) 5512-5532, with the only difference that the excess of thionyl chloride is removed before quenching by distillation. Although the yield of 86% is very much improved in this case, the disadvantages of using a base (solid potassium hydroxide in this case) and the multiple extraction with large amounts of chloroform remain.

Another method for dehydrating isonipecotamide is described in US 2006/0084808A1. Here, isonipecotamide is likewise dehydrated by heating in excess thionyl chloride (4 to 15 mol equivalents). The workup consists of taking up the entire reaction mixture in water, adjusting the pH to 12 to 13 with NaOH, repeated extraction of the resulting solution with benzene, toluene or xylene, distilling off the extracting agent and distillation of the product; the stated yields are between 32.7 and 62.8%. The disadvantages here in turn are the necessity to use a large amount of base to adjust to the desired pH; the multiple extraction with a solvent which must then be removed by distillation; the distillation of the product and the low to moderate yield. The yields described could not be reproduced. After repeated attempts, the isolation of product was basically not possible.

In all methods described to date, the product, 4-cyanopiperidine, is isolated as the free base which is difficult due to the high water solubility thereof. The disadvantage of these methods is therefore that either a low yield or the use of large amounts of solvents for the extraction must be taken into account.

A method which has become known from WO 2004/092124 for preparing 4-cyanopiperidine hydrochloride consists of dehydrating isonipecotamide with phosphorus oxychloride, adding water to the reaction mixture, adjusting the pH to 12 with aqueous sodium hydroxide solution, reacting with di-tert-butyl dicarbonate, extracting the resulting 4-cyano-1-tertbutoxycarbonylpiperidine with ethyl acetate, removing the solvent, purifying the crude product by chromatography on silica gel, and finally removing the Boc residue (Boc=tertbutoxycarbonyl) by means of HCl in dioxane. In addition to the disadvantages already mentioned above (amounts of bases and solvent; laborious workup steps), this method has the disadvantage that three steps are required for preparing 4-cyanopiperidine hydrochloride starting from isonipecotamide. All known methods for preparing 4-cyanopiperidine hydrochloride via the 4-cyano-1-tert-butoxycarbonylpiperidine have this disadvantage.

This also applies to a method which has become known from US 2006/0173050 for preparing 4-cyanopiperidine trifluoroacetate. In this case, isonipecotamide is firstly reacted with di-tert-butyl dicarbonate; it is then dehydrated using a mixture of imidazole and phosphorus oxychloride and the Boc residue is finally cleaved by reaction with trifluoroacetic acid. The overall yield for all three stages is only 54.7% of theory.

SUMMARY

By reason of the disadvantages described above, the object therefore also consisted of providing an advantageous method of preparing 4-cyanopiperidine, technically simple to carry out and both economical and ecological. This object was achieved by producing 4-cyanopiperidine hydrochloride, by means of a suitable procedure, which was present in a reaction mixture from which it was simple to isolate. The method may be described as follows:

It has been found that 4-cyanopiperidine hydrochloride (I)

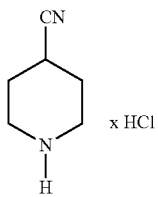

(I)

can be prepared in high yield and with high purity, characterized in that isonipecotamide (II)

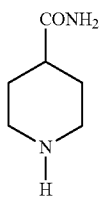

(II)

is dehydrated with thionyl chloride in a diluent in the presence of a formamide of general formula (III), wherein the formamide of general formula (III) is defined as follows:

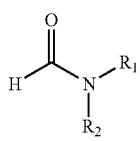

(III)

$R^1$, $R^2$ are mutually independently hydrogen, $C_1$-$C_6$-alkyl, $C_6$-$C_{10}$-aryl or together form a —$CH_2$—$CH_2$—$X_n$—$CH_2$—$CH_2$— residue, in which
X is $CH_2$, oxygen or sulphur
and
n is 0 or 1.

DETAILED DESCRIPTION OF A PREFERRED EMBODIMENT

Preference is given to a method according to the invention in which the residues of formula (III) are defined as follows:
$R^1$, $R^2$ are mutually independently hydrogen, methyl, ethyl, 1-propyl, 2-propyl, 1-butyl, 2-butyl, isobutyl, tertiary butyl or together form a —$CH_2$—$CH_2$—$X_n$—$CH_2$—$CH_2$ residue;
X is $CH_2$ or oxygen,
and
n is 0 or 1.

Particular preference is given to a method according to the invention in which the residues of formula (III) are defined as follows:
$R^1$, $R^2$ are 1-butyl.

Method Description

The method according to the invention for preparing 4-cyanopiperidine hydrochloride (I) can be illustrated by the scheme below:

Scheme 1:

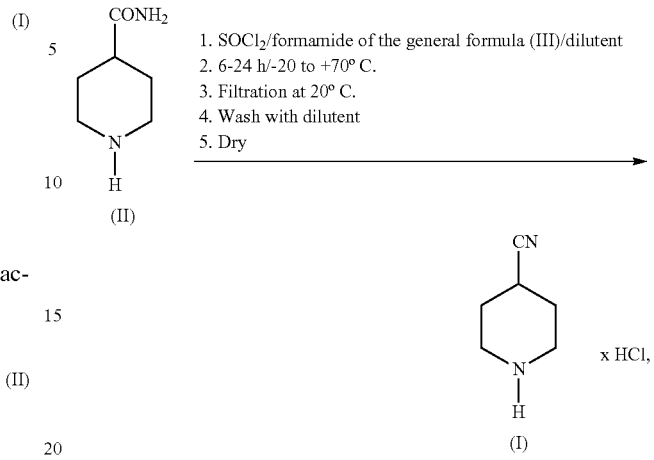

wherein the formamide of general formula (III) is as defined above.

Formamides of general formula (III) include, for example, but are not limited to: formamide, dimethylformamide (DMF), diethylformamide, ethylmethylformamide, di-n-propylformamide, dibutylformamide (DBF), dihexylformamide, N-formylpyrrolidine, N-formylpiperidine, N-formylmorpholine, N-formylthiomorpholine.

Preference is given to using dimethylformamide (DMF), dibutylformamide (DBF), N-formylpiperidine and N-formylmorpholine.

Particular preference is given to using dibutylformamide (DBF).

The amount of formamide of general formula (III) can be varied within wide limits. Preference is given to using 0.1 to 3 mol equivalents, based on isonipecotamide. Particular preference is given to using 0.3 to 2 mol equivalents, and particular preference to 0.5 to 1.5 mol equivalents.

The amount of thionyl chloride in the method according to the invention is typically 1 to 5 mol equivalents, based on isonipecotamide. Preference is given to using 1.5 to 3.5 mol equivalents of thionyl chloride, and particular preference to 2 to 3 mol equivalents.

Although a dehydrating agent is used in the method according to the invention with thionyl chloride, it is advantageous that the isonipecotamide used is of high purity, particularly in relation to the water content. Preference is given to using isonipecotamide having a water content of less than 5%, particularly preferably having a water content of less than 2%.

Water-containing isonipecotamide can be dried by generally known methods, for example, by heating in a vacuum, by azeotropic distillation with an organic solvent, or by drying over a drying agent such as phosphorus pentoxide. For the azeotropic drying, useful solvents include, for example, toluene, ortho-xylene, n-propyl acetate or n-butyl acetate.

In principle, all organic diluents or diluent mixtures inert under the reaction conditions are suitable as diluents for the method according to the invention. Examples include, but are not limited to: ketones such as acetone, diethyl ketone, methyl ethyl ketone and methyl isobutyl ketone; nitriles such as acetonitrile and butyronitrile; ethers such as dimethoxyethane (DME), tetrahydrofuran (THF), 2-methyl-THF and 1,4-dioxane; hydrocarbons and halogenated hydrocarbons such as hexane, heptane, cyclohexane, methylcyclohexane, toluene, ortho-xylene, meta-xylene, para-xylene, mesitylene, chlorobenzene, ortho-dichlorobenzene or nitrobenzene; esters such as methyl acetate, ethyl acetate, n-propyl acetate, isopropyl acetate, n-butyl acetate, isobutyl acetate, sec-butyl acetate, hexyl acetate, cyclohexyl acetate, (2-ethylhexyl) acetate.

The diluent is preferably selected from the group comprising aromatic hydrocarbons, chlorinated aromatic hydrocarbons and esters, or mixtures of these diluents.

Particular preference is given to toluene, ortho-xylene, meta-xylene, para-xylene, chlorobenzene, methyl acetate, ethyl acetate, n-propyl acetate, isopropyl acetate, n-butyl acetate, isobutyl acetate, sec-butyl acetate, hexyl acetate, cyclohexyl acetate, (2-ethylhexyl) acetate or mixtures of these diluents.

Very particular preference is given to using the diluents toluene, ortho-xylene, meta-xylene para-xylene, methyl acetate, ethyl acetate, n-propyl acetate, isopropyl acetate, n-butyl acetate or mixtures of these diluents.

The temperature of the method according to the invention can be varied within wide limits. The method is typically carried out at a temperature between −20 and +70° C., preferably at a temperature between 0 and +50° C., particularly preferably at a temperature between +10 and +30° C.

The reaction time of the method according to the invention can be varied within wide limits. It is typically 6 to 24 hours.

The method according to the invention is typically carried out at atmospheric pressure. However, it may also be carried out at reduced or elevated pressure.

The 4-cyanopiperidine hydrochloride is isolated in the method according to the invention in such a way that the product is isolated as a solid by filtration of the reaction mixture, this solid is purified by washing with the diluent used in the reaction and is subsequently either dried or is dissolved or suspended directly in the solvent required for a subsequent reaction.

In this manner, 4-cyanopiperidine hydrochloride is obtained by the method according to the invention in high yield and purity.

The method according to the invention is to be illustrated by the examples which follow, without being limited thereto.

Example 1

11.9 g [75.7 mmol] of dibutylformamide (99%) were added to a suspension of 10 g [75.7 mmol] of isonipecotamide (97%) in 50 ml of n-propyl acetate at 20° C. over 5 minutes. After 5 minutes, the addition of 18.91 g [158.9 mmol] of thionyl chloride at 20° C. was initiated. This addition required 45 minutes in which the temperature was maintained constantly at 20° C. After the end of the addition, the mixture was stirred at 20° C. for a further 18 hours. The suspension was filtered and the filter residue was washed with n-propyl acetate. After drying there remained 8.55 g of a colourless solid. Analysis by quantitative NMR spectroscopy gave a 4-cyanopiperidine hydrochloride content of 95% (w/w). A yield of 73% of theory is calculated therefrom.

Chloride content by ion chromatography (IC): 26.4% (calc.: 24.8%).

$^1$H-NMR (600 MHz, $d_6$-DMSO): δ=1.91-2.13 (m, 2H), 2.08-2.13 (m, 2H), 2.97-3.00 (m, 2H), 3.12-3.2 (m, 3H), 9.27 (s, br, 2H) ppm.

Example 2

In a 1 liter jacketed vessel, 111.56 g [0.702 mol] of dibutylformamide (99%) were added to a suspension of 92.8 g [0.702 mol] of isonipecotamide (97%) in 450 ml of n-propyl acetate at 20° C. over 10 minutes. After 5 minutes, the addition of 175.46 g [1.475 mol] of thionyl chloride at 20° C. was initiated. This addition required 60 minutes in which the temperature was maintained constantly at 20° C. After the end of the addition, the mixture was stirred at 20° C. for a further 18 hours. The suspension was released from the reactor and filtered. The filter cake was washed three times each with 150 ml of n-propyl acetate and then dried. 83.07 g of a colourless solid were obtained. Analysis by GC against a reference standard following silylation gave a 4-cyanopiperidine hydrochloride content of 98.1% (w/w). A yield of 79.1% of theory is calculated therefrom.

Example 3

In a 1 liter jacketed vessel, 111.56 g [0.702 mol] of dibutylformamide (99%) were added to a suspension of 92.8 g [0.702 mol] of isonipecotamide (97%) in 450 ml of n-propyl acetate at 20° C. over 10 minutes. After 5 minutes, the addition of 175.46 g [1.475 mol] of thionyl chloride at 20° C. was initiated. This addition required 60 minutes in which the temperature was maintained constantly at 20° C. After the end of the addition, the mixture was stirred at 20° C. for a further 18 hours. The suspension was released from the reactor and filtered. The filter cake was washed three times each with 150 ml of n-propyl acetate and then dissolved in 532 g of methanol. From the resulting 681.2 g of solution, 10 g were concentrated under vacuum from which 1.2 g of colourless solid were obtained as residue. Analysis by GC against a reference standard following silylation gave a 4-cyanopiperidine hydrochloride content of 98.5% (w/w). A yield of 78.1% of theory is calculated therefrom.

Example 4

56.8 g [56.8 mmol] of dibutylformamide (99%) were added to a suspension of 10 g [75.7 mmol] of isonipecotamide (97%) in 50 ml of n-propyl acetate at 20° C. over 5 minutes. After 5 minutes, the addition of 18.91 g [158.9 mmol] of thionyl chloride at 20° C. was initiated. This addition required 45 minutes in which the temperature was maintained constantly at 20° C. After the end of the addition, the mixture was stirred at 20° C. for a further 18 hours. The suspension was filtered and the filter residue was washed with n-propyl acetate. After drying there remained 9.92 g of a colourless solid. Analysis by GC against a reference standard following silylation gave a 4-cyanopiperidine hydrochloride content of 95.9% (w/w). A yield of 85.7% of theory is calculated therefrom.

Example 5

11.9 g [75.7 mmol] of dibutylformamide (99%) were added to a suspension of 10 g [75.7 mmol] of isonipecotamide (97%) in 50 ml of toluene at 20° C. over 5 minutes. After 5 minutes, the addition of 18.91 g [158.9 mmol] of thionyl chloride at 20° C. was initiated. This addition required 45 minutes in which the temperature was maintained constantly at 20° C. After the end of the addition, the mixture was stirred at 20° C. for a further 18 hours. The suspension was filtered and the filter residue was washed with toluene. After drying there remained 9.63 g of a colourless solid. Analysis by GC against a reference standard following silylation gave a 4-cyanopiperidine hydrochloride content of 99.7% (w/w). A yield of 86.5% of theory is calculated therefrom.

Example 6

In a 1 liter jacketed vessel, 111.56 g [0.702 mol] of dibutylformamide (99%) were added to a suspension of 92.8 g [0.702 mol] of isonipecotamide (97%; water content: 0.95%) in 450 ml of toluene at 20° C. over 10 minutes. After 5 minutes, the addition of 175.46 g [1.475 mol] of thionyl chloride at 20° C. was initiated. This addition required 60 minutes in which the temperature was maintained constantly at 20° C. After the end of the addition, the mixture was stirred at 20° C. for a further 18.5 hours. The suspension was released from the reactor and filtered. The filter cake was washed three times each with 150 ml of toluene and then dried. 79.92 g of a colourless solid were obtained. Analysis by GC against a reference standard following silylation gave a 4-cyanopiperidine hydrochloride content of 98.4% (w/w). A yield of 76.4% of theory is calculated therefrom.

Example 7

To a stirred suspension of 5 g [39 mmol] of isonipecotamide and 12.3 g [78.0 mmol] of dibutylformamide in 29 ml of toluene were added dropwise 13.9 g [117 mmol] of thionyl chloride at 0° C. over 15 min, whereupon the temperature increased up to 10° C. The mixture was then stirred at 0° C. for 3 days. The suspension was filtered off and the filter residue was washed with toluene. After drying under vacuum, 4.43 g of a colourless solid were obtained. Analysis by GC against a reference standard following silylation gave a 4-cyanopiperidine hydrochloride content of 96.4% (w/w). A yield of 74.7% of theory is calculated therefrom.

Example 8

To a stirred suspension of 5 g [39 mmol] of isonipecotamide and 0.29 g [3.9 mmol] of dimethylformamide in 40 ml of n-propyl acetate were slowly added dropwise 13.9 g [117 mmol] of thionyl chloride at 10° C., whereupon the temperature increased up to 15° C. The mixture was then stirred at 20° C. for 38 hours. A further 1.16 g [15.6 mmol] of dimethylformamide were then added, and the mixture was stirred at 20° C. for a further 21 h. The suspension was filtered off and the filter residue was washed with n-propyl acetate. After drying under vacuum at 50° C., 4.55 g of a beige solid were obtained. Analysis by GC against a reference standard following silylation gave a 4-cyanopiperidine hydrochloride content of 92.2% (w/w). A yield of 73.3% of theory is calculated therefrom.

Example 9

To a stirred suspension of 10 g [78 mmol] of isonipecotamide and 12.3 g [78.0 mmol] of dibutylformamide in 50 ml of n-butyl acetate were slowly added dropwise 19.5 g [163 mmol] of thionyl chloride at 20° C., whereupon the temperature increased up to 30° C. The mixture was then stirred at 20° C. for 20 hours. The suspension was filtered off and the filter residue was washed with n-butyl acetate. After drying under vacuum, 10.8 g of a colourless solid were obtained. Analysis by GC against a reference standard following silylation gave a 4-cyanopiperidine hydrochloride content of 81.7% (w/w). A yield of 77.1% of theory is calculated therefrom.

Comparative Example 1 (According to the Procedure in US 2006/0084808 A1)

At the start, 10 g [75.7 mmol] of isonipecotamide (97%) were added in portions to 23.2 g [195 mmol] of thionyl chloride at 20° C., whereupon the temperature increased to 35° C. Already after addition of about 2 g of the isonipecotamide, a viscous, sticky lump formed which adhered to the wall of the flask and even with relatively rapid stirring could not be detached and comminuted. The experiment therefore had to be terminated

The invention claimed is:

1. A method for preparing 4-cyanopiperidine hydrochloride of formula (I),

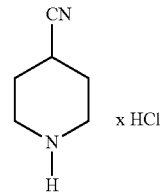

(I)

in high yield and with high purity, wherein isonipecotamide (II)

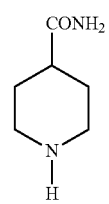

(II)

is dehydrated with thionyl chloride in a diluent in the presence of a formamide of formula (III), wherein the formamide of formula (III) is defined as follows:

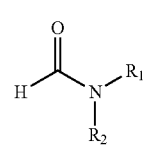

(III)

$R^1$, $R^2$ are mutually independently hydrogen, $C_1$-$C_6$-alkyl, $C_6$-$C_{10}$-aryl or together form a —$CH_2$—$CH_2$—$X_n$—$CH_2$—$CH_2$— residue, in which X is $CH_2$, oxygen or sulphur and n is 0 or 1, and wherein the diluent is toluene, ortho-xylene, meta-xylene, para-xylene, methyl acetate, ethyl acetate, n-propyl acetate, isopropyl acetate, n-butyl acetate or mixtures thereof.

2. A method according to claim 1, wherein the formamide of formula (III) is defined as follows:

$R^1$, $R^2$ are mutually independently hydrogen, methyl, ethyl, 1-propyl, 2-propyl, 1-butyl, 2-butyl, isobutyl, tertiary butyl or together form a —$CH_2$—$CH_2$—$X_n$—$CH_2$—$CH_2$— residue;

X is $CH_2$ or oxygen, and n is 0 or 1.

3. A method for preparing 4-cyanopiperidine hydrochloride of formula (I),

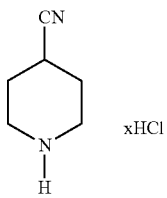

in high yield and with high purity, wherein isonipecotamide (II)

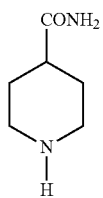

is dehydrated with thionyl chloride in a diluent in the presence of a formamide of formula (III), wherein the formamide of formula (III) is defined as follows:

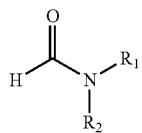

$R^1$, $R^2$ are 1-butyl.

4. A method according to claim 1, wherein 1 to 5 mol equivalents of thionyl chloride are used, based on isonipecotamide.

5. A method according to claim 1, wherein 0.1 to 3 mol equivalents of formamide are used, based on isonipecotamide.

6. A method according to claim 1, wherein the reactant isonipecotamide has a water content of less than 5%.

7. A method according to claim 3, wherein the diluent is toluene, ortho-xylene, meta-xylene, para-xylene, methyl acetate, ethyl acetate, n-propyl acetate, isopropyl acetate, n-butyl acetate or mixtures thereof.

8. A method according to claim 1, wherein the yield of the 4-cyanopiperidine hydrochloride is at least 73%.

9. A method according to claim 1, wherein the purity of the 4-cyanopiperidine hydrochloride is at least 81%.

10. A method according to claim 1, wherein one or both of $R^1$ and $R^2$ are hydrogen.

11. A method according to claim 1, wherein one or both of $R^1$ and $R^2$ are mutually independently $C_1$-$C_6$-alkyl.

12. A method according to claim 1, wherein one or both of $R^1$ and $R^2$ are mutually independently $C_6$-$C_{10}$-aryl.

13. A method according to claim 1, wherein $R^1$ and $R^2$ together form a —$CH_2$—$CH_2$—$X_n$—$CH_2$—$CH_2$.

14. A method according to claim 13, wherein:
n is 0.

15. A method according to claim 13, wherein:
n is 1.

16. A method according to claim 15, wherein:
X is $CH_2$.

17. A method according to claim 15, wherein:
X is oxygen.

18. A method according to claim 15, wherein:
X is sulphur.

19. A method according to claim 1, wherein the diluent is toluene, n-propyl acetate, or n-butyl acetate.

20. A method according to claim 1, wherein the reactant isonipecotamide has a water content of less than 2%.

* * * * *